United States Patent
Chen et al.

(10) Patent No.: US 9,375,402 B2
(45) Date of Patent: Jun. 28, 2016

(54) ORAL FORMULATIONS OF KINASE INHIBITORS

(71) Applicant: VERASTEM, INC., Needham, MA (US)

(72) Inventors: Andrew Xian Chen, San Diego, CA (US); Yali J. Tsai, La Jolla, CA (US)

(73) Assignee: VERASTEM, INC., Needham, MA (US)

(*) Notice: Subject to any disclaimer, the term of this patent is extended or adjusted under 35 U.S.C. 154(b) by 0 days.

(21) Appl. No.: 13/967,270

(22) Filed: Aug. 14, 2013

(65) Prior Publication Data

US 2014/0206692 A1 Jul. 24, 2014

Related U.S. Application Data

(63) Continuation of application No. 13/807,638, filed as application No. PCT/US2011/042162 on Jun. 28, 2011, now abandoned.

(60) Provisional application No. 61/359,694, filed on Jun. 29, 2010.

(51) Int. Cl.
| | | |
|---|---|---|
| *A61K 31/44* | (2006.01) | |
| *A61K 31/435* | (2006.01) | |
| *A61K 9/107* | (2006.01) | |
| *A61K 31/5377* | (2006.01) | |
| *C07D 213/74* | (2006.01) | |

(52) U.S. Cl.
CPC ............. *A61K 9/107* (2013.01); *A61K 31/5377* (2013.01); *C07D 213/74* (2013.01); *A61K 31/435* (2013.01)

(58) Field of Classification Search
CPC . A61K 31/435; A61K 31/44; A61K 31/5375; A61K 31/5377
USPC .................................................. 514/277, 282
See application file for complete search history.

(56) References Cited

U.S. PATENT DOCUMENTS

| | | | |
|---|---|---|---|
| 4,656,182 | A | 4/1987 | Horwell |
| 2004/0006005 | A1 | 1/2004 | Bhanot |
| 2005/0090515 | A1 | 4/2005 | Pease et al. |
| 2008/0119515 | A1 | 5/2008 | Siddiqui et al. |
| 2008/0193518 | A1 | 8/2008 | Zarkadas et al. |
| 2009/0203709 | A1 | 8/2009 | Steinberg et al. |
| 2010/0317663 | A1 | 12/2010 | Adams et al. |

FOREIGN PATENT DOCUMENTS

| | | |
|---|---|---|
| CN | 1335838 A | 2/2002 |
| CN | 101119976A A | 2/2008 |
| WO | 0039101 A1 | 7/2000 |
| WO | 0230414 A1 | 4/2002 |
| WO | 2004002410 A2 | 1/2004 |
| WO | 2006/053755 A1 | 5/2006 |
| WO | 2006087387 A1 | 8/2006 |
| WO | 2007050574 A1 | 5/2007 |
| WO | 2008/011154 A2 | 1/2008 |
| WO | 2008/115369 A2 | 9/2008 |
| WO | 2009/105498 A1 | 8/2009 |
| WO | 2009153589 A1 | 12/2009 |
| WO | 2011019943 A1 | 2/2011 |
| WO | 2011133668 A2 | 10/2011 |

OTHER PUBLICATIONS

Guan, "Role of Focal Adhesion Kinase in Integrin Signaling", Int J Biochem Cell Biol., 29(8-9), pp. 1085-96, (1997).
H Sawai, et al. (2005), "Activation of focal adhesion kinase enhances the adhesion and invasion of pancreatic cancer cells via extracellular signal-regulated kinase-1/2 signaling pathway activation" Molecular Cancer, 4:37.
International Preliminary Report on Patentability for PCT/US2011/42162 dated Jan. 8, 2013.
International Search Report for PCT/US2011/42162 dated Nov. 4, 2011.
Written Opinion for PCT/US2011/42162 dated Nov. 4, 2011.
Supplementary European Search Report for Application No. EP11804122 dated Oct. 31, 2014.
European Search Report for European Application No. 10808776.8 dated Dec. 12, 2012.
European Search Report for European Application No. 11810100.5 Dated Jun. 23, 2014.
International Search Report for PCT/US 11/42169, dated Jun. 28, 2011.
Lietha et al., Crystal Structres of the FAK Finase in Complex with TAE226 and Related Bis-Anilino Pyrimidine Inhibitors Reveal a Helical DFG Confromation. PLos ONE, Nov. 2008, vol. 3, Iss 11, pp. 1-11.
Schaller et al, "PND-1186 FAK inhibitor selectively promotes tumor cell apoptosis in three dimensional environments" Cancer Biology & Therapy, vol. 9, No. 10, May 15, 2010, pp. 791-793.
Search Report & Written Opinion for PCT/US2010/045359, mailed Oct. 5, 2010.
Tanjoni et al. "PND-1186 FAK inhibitor selectively promotes tumor cell apoptosis in three dimensional environments" Cancer Biology & Therapy, vol. 9, No. 10, May 15, 2010, pp. 764-777.
Walsh et al. "Oral delivery of PND-1186 FAK inhibitor decreases tumor growth and spontaneous breast to lunch metastasis in preclinical models", Cancer Biology & Therapy, vol. 9, No. 10, May 15, 2010, pp. 778-790.
Written Opinion for PCT/US 11/42169, dated Jun. 28, 2011.

*Primary Examiner* — Kevin E Weddington
(74) *Attorney, Agent, or Firm* — Lando & Anastasi, LLP

(57) ABSTRACT

The invention is directed to formulations of bioactive compounds of limited water solubility, inhibitors of focal adhesion kinase (FAK) of the 2,4-diaminopyridine class, adapted for oral administration to patients. The formulations are self-emulsifying in the gastrointestinal tract of the patients, providing enhanced absorption and bioavailability of the bioactive compounds as dispersions or emulsions in an oil base. For example, esters of PEG-ylated glycerol can be used as the oil, in conjunction with surfactants such as lecithin and TEPG succinate and solubilizers such as PEG 400 to provide useful oral formulations for administration to patients having a malcondition wherein inhibition of FAK is medically indicated, such as cancer or arthritis.

4 Claims, No Drawings

ORAL FORMULATIONS OF KINASE INHIBITORS

CROSS-REFERENCE TO RELATED APPLICATIONS

This application Continuation of Ser. No. 13/807,638, filed Dec. 28, 2012 which is a National Stage Application under 35 U.S.C. §371 from PCT/US2011/042162, filed Jun. 28, 2011, published as WO 2012/006081 on Jan. 12, 2012, which claims the priority of U.S. provisional application Ser. No. 61/359,694, filed Jun. 29, 2010, each of which is incorporated by reference herein in its entirety.

BACKGROUND

Small-molecule inhibitors of various classes of kinases have become significant exploratory medicinal compounds. However, certain kinase inhibitors possess properties of low water solubility and poor oral bioavailability.

Among the various classes of kinases for which experimental small-molecule inhibitors have been developed are the family known as Focal Adhesion Kinase. Focal adhesion kinase (FAK) has recently been established as a key component of the signal transduction pathways triggered by integrins. Aggregation of FAK with integrins and cytoskeletal proteins in focal contacts has been proposed to be responsible for FAK activation. Recent results from a number of different approaches have shown that integrin signaling through FAK leads to increased cell migration on fibronectin as well as potentially regulating cell proliferation and survival. J L Guan (1997 August-September), *Int J Biochem Cell Biol.*, 29(8-9): 1085-96. Interaction with integrin and focal adhesion kinase (FAK) regulates the cancer cell adhesion and invasion into extracellular matrix (ECM). In addition, phosphorylation of FAK correlates with the increase of cell motility and invasion. Adhesion and spreading of cancer cells on a variety of ECM proteins, including collagen type IV, leads to an increase in tyrosine phosphorylation and activation of FAK. H Sawai, et al. (2005), *Molecular Cancer*, 4:37.

Certain compounds of the 2,4-diaminopyridine class of inhibitors show promise in the treatment of malconditions that may be affected by FAK, such as proliferative disorders such as cancer and inflammatory disorders such as arthritis. See, for example, published PCT application WO2008/115369, wherein compounds of this type are disclosed. For effective therapeutic use, such compounds must be formulated to provide adequate pharmacokinetic properties, such as AUC. Oral administration of compounds is generally preferred by the patient population, so oral formulations providing favorable pharmacokinetics are needed.

SUMMARY

The invention is directed to formulations of kinase inhibitors, such as small-molecule inhibitors of Focal Adhesion Kinase, adapted for oral administration to patients. In various embodiments, the oral formulations are self-emulsifying formulations adapted to provide favorable pharmacokinetic properties for compound often of limited water solubility.

In various embodiments, the invention provides an oral formulation for administration of a kinase inhibitor, comprising
(a) the kinase inhibitor in pharmaceutically acceptable form;
(b) an oil;
(c) a solubilizer; and
(d) a surfactant.

In various embodiments, the invention provides a method for treatment of a malcondition in a patient wherein inhibition of a kinase is medically indicated, comprising orally administering to the patient an effective amount the formulation of the invention in a dose, at a frequency and for a duration of time to provide a beneficial effect to the patient.

In various embodiments, the invention provides a method of preparing the formulation of the invention, comprising combining the kinase inhibitor and the solubilizing agent and, optionally, an organic solvent, then combining with the oil and the surfactant.

DETAILED DESCRIPTION

The term "about" as used herein, when referring to a numerical value or range, allows for a degree of variability in the value or range, for example, within 10%, or within 5% of a stated value or of a stated limit of a range.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein Focal Adhesion Kinase (FAK) plays a role in the biochemical mechanisms involved in the disease or malcondition such that a therapeutically beneficial effect can be achieved by acting on the kinase. "Acting on" FAK can include binding to FAK and/or inhibiting the bioactivity of FAK.

"Administering" or "administration" refers to providing a medicinal compound to a patient in need thereof. A "dose" is the amount of the active pharmaceutical ingredient (API), in this case picoplatin, that is provided in a single administration. A "frequency" of administration refers to how often the medication is given when repeated doses are prescribed; for example, the medication can be administered daily. A "duration" refers to the period of time over which repeated doses are administered; for example, the picoplatin can be administered for a duration of two weeks.

The expression "effective amount", when used to describe therapy to an individual suffering from a disorder, refers to the amount of a compound of the invention that is effective to inhibit or otherwise act on FAK in the individual's tissues wherein FAK involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

A "formulation" as the term is used herein is a composition of matter including picoplatin and other components, such as excipients, stabilizers, dispersants, surfactants, and the like.

"Self-emulsifying" refers to a property of a formulation wherein upon contacting the formulation with an aqueous medium, such as in the gastro-intestinal tract of a patient, the formulation spontaneously forms an emulsion.

An "oil" as the term is used herein refers to an organic liquid, which is water-insoluble, or at least only partially water-soluble, that can form a separate phase in the presence of water. An example of an "oil" is a glyceride such as a medium chain triglyceride, or a medium chain mono- or di-glyceride, or castor oil. Another example of an oil is a fatty ester. A fatty ester refers to an alkyl ester of a fatty acid. An example is ethyl oleate. "MCT oil" refers to medium chain triglyceride oil. Examples include the MCT oil sold under the Miglyol trademark, such as Miglyol 912, a caprylate/caprate (octanoate/decanoate triglyceride).

"Miglyol 812" (Sasol Germany GmbH, Witten, Germany) refers to a medium chain triglyceride wherein the acid moieties are caprylic and capric acid. Miglyol is a trademark identifying the source of this and other varieties of MCT oil.

"Capmul MCM" is a glyceryl caprate/caprylate ester.

"Labrafil M 2125" is a linoleoyl PEG-glyceride, i.e., a linoleic ester of PEG-ylated glycerol.

A "surfactant" as the term is used herein is a substance that reduces interfacial surface tension between immiscible liquids such as oil and water, reduces surface tension of a water drop, and exhibits other surface-active properties as are well known in the art. Surfactants are also known as "emulsifiers."

The term "weight average molecular weight" is well known in the art and characterizes an average molecular weight of a polydisperse sample of a polymer.

A "PEG" or a "polyethyleneglycol" is a polymeric material composed of repeating —CH$_2$CH$_2$O— units, wherein there are two or more units. Thus, diethyleneglycol and all higher polymers are polyethyleneglycols within the meaning herein. A polyethyleneglycol can have a free OH group at either terminus or at both termini, or can alternatively include other groups such as an ether group at one or both ends, for example a dimethyl ether CH$_3$O—(CH$_2$CH$_2$O)$_n$—OCH$_3$ or a monomethyl ether CH$_3$O—(CH$_2$CH$_2$O)$_n$—OH. Such an ether-terminated PEG can also be referred to as a "polyethyleneglycol ether". PEG-400 is a PEG with a weight average molecular weight of about 400 DA. PEG-8000 is a PEG with a weight average molecular weight of about 8000 DA. A compound can be "PEG-ylated", meaning that it bears at least one PEG group, which can be introduced in a variety of ways, such as by polymerization of ethylene glycol initiated by the compound, or coupling of the compound with a preformed PEG.

"Polysorbate 80" refers to sorbitan mono-9-octadecanoate poly(oxy-1,2-ethanediyl) derivatives; they are well known as complex mixtures of polyoxyethylene ethers used as emulsifiers or dispersing agents in pharmaceuticals.

"Sodium Lauryl Sulfate" is sodium dodecyl sulfate, a well known commercially available surfactant.

"Phospholipon 90G" or "PL90G" (American Lecithin Products, Oxford, Conn.) is a tradename for lecithin, minimum 94% phosphatidylcholine for the manufacture of liposomes. "Phospholipon 90H" or "PL90H" is a hydrogenated PL90G. The term "PL90" refers to either one of these materials.

"Vitamin E TPGS" refers to the compound D-alpha-tocopheryl polyethylene glycol 1000 succinate.

In various embodiments, the invention provides an oral formulation for administration of a kinase inhibitor, comprising (a) the kinase inhibitor in pharmaceutically acceptable form;

(b) an oil;

(c) a solubilizer; and (d) a surfactant.

For example, the formulation can comprise about 0.01 wt % to about 20 wt % of the kinase inhibitor. More specifically, the formulation can comprise about 2 wt % to about 7 wt % of the kinase inhibitor. In various embodiments, the kinase inhibitor can be of formula (I)

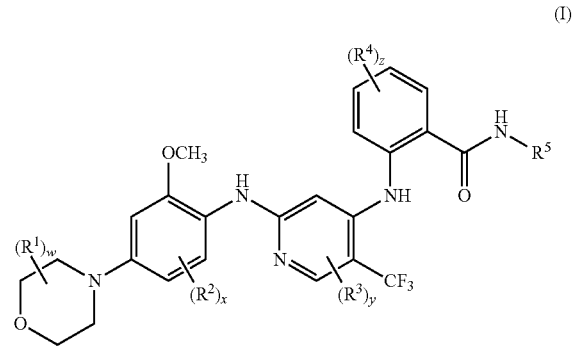

(I)

wherein $R^1$ is alkyl, aryl, cycloalkyl, heterocyclyl, aryl, or heteroaryl;

$R^2$, $R^3$ and $R^4$ are each independently alkyl, aryl, cycloalkyl, heterocyclyl, aryl, heteroaryl, alkoxy, aryloxy, or fluoro;

$R^5$ is hydrogen, alkyl, aryl, cycloalkyl, heterocyclyl, aryl, or heteroaryl;

w is 1 to 4;

x is 1 to 3;

y is 1 to 2; and z is 1 to 4;

or any pharmaceutically acceptable salt thereof.

More specifically, the kinase inhibitor can be of the formula

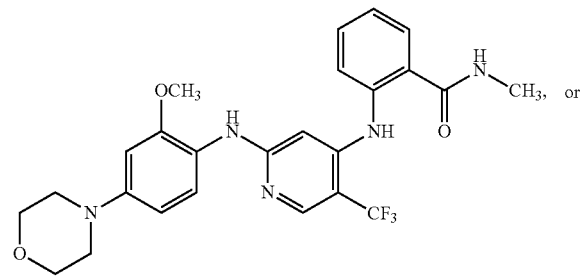

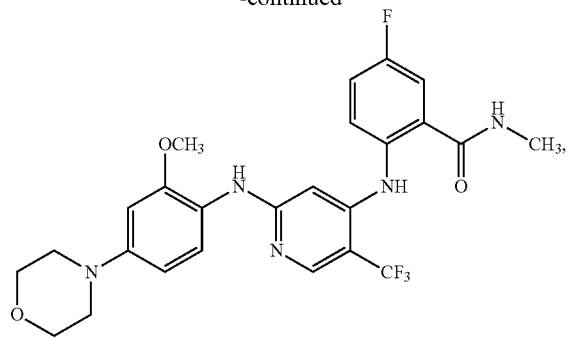

or any pharmaceutically acceptable salt thereof.

In various embodiments, the formulation can comprise about 20 wt % to about 80 wt % of the oil. The oil can be a composition selected from the set consisting of a medium chain triglyceride wherein the acid moieties are caprylic and capric acid (such as Migloyl 812), a glyceryl caprate/caprylate ester (such as Capmul MCM), a linoleoyl PEG-glyceride (such as Labrafil M 1944 CS), castor oil, and oleic acid. Preferably, the oil is a glyceryl caprate/caprylate ester such as Capmul MCM.

In various embodiments, the formulation can comprise about 5 wt % to about 50 wt % of the solubilizer. In various embodiments the solubilizer can comprise ethanol, isopropanol, propylene glycol, PEG 400, or glycerol, or any combination thereof; optionally additionally comprising sodium lauryl sulfate (sodium dodecyl sulfate), polysorbate 80 (sorbitan mono-9-octadecanoate poly(oxy-1,2-ethanediyl) derivatives), or a combination thereof. Preferably, the solubilizer comprises PEG 400, for example the formulation can comprise up to about 10% PEG 400.

In various embodiments, the formulation can comprise about 5 wt % to about 50 wt % of the surfactant. In various embodiments, the surfactant can comprises a lecithin such as Phospholipon 90G, an alpha-tocopheryl polyethylene glycol 1000 succinate (Tocopheryl polyethylene glycol 400), or any combination thereof. For example, the surfactant can comprise a mixture a lecithin such as Phospholipon 90G and an alpha-tocopheryl polyethylene glycol 1000 succinate such as Tocopheryl polyethylene glycol 400. More specifically, the surfactant comprise an approximately 1:1 mixture of a lecithin such as Phospholipon 90G and an alpha-tocopheryl polyethylene glycol 1000 succinate such as Tocopheryl polyethylene glycol 400.

In various embodiments, a formulation of the invention can comprise about 2 wt % to about 5 wt % of the kinase inhibitor, about 35-50 wt % of a glyceryl caprate/caprylate ester (such as Capmul MCM), about 20-40 wt % of a lecithin such as Phospholipon 90G, about 15-30 wt % of an -alpha-tocopheryl polyethylene glycol 1000 succinate such as Tocoperyl polyethylene glycol 1000 succinate, and up to about 10% PEG 400.

In various embodiments, the kinase inhibitor can be present in a formulation of the invention in free base form. In other embodiments, the kinase inhibitor can be a pharmaceutically acceptable salt of the inhibitor, such as a hydrochloride salt. In various embodiments, the kinase inhibitor can be SR3721, SR2516, or SR3406, the structures of which are shown below.

In various embodiments, the formulation can be self-emulsifying in an aqueous medium. For example, the formulation can be self-emulsifying in the gastrointestinal tract of a patient ingesting the formulation.

In various embodiments, a formulation of the invention, upon oral ingestion by a patient, can increase the pharmacokinetic parameter Area Under the Curve (AUC) in the patient relative to the AUC for a comparable dose of the same kinase inhibitor orally administered in a non-self-emulsifying formulation. In various embodiments, the invention provides a method for treatment of a malcondition in a patient wherein inhibition of a kinase is medically indicated, comprising orally administering to the patient an effective amount the formulation of the invention in a dose, at a frequency and for a duration of time to provide a beneficial effect to the patient. In various embodiments, the malcondition comprises a proliferative disorder such as cancer or an inflammatory disorder such as arthritis.

In various embodiments, the invention provides the use of a formulation of the invention for treatment of a malcondition. For example, the malcondition can comprise a proliferative disorder such as cancer or an inflammatory disorder such as arthritis.

In various embodiments, the invention provides a method of preparing a formulation of the invention, the method comprising combining the kinase inhibitor and the solubilizing agent and, optionally, an organic solvent, then combining with the oil and the surfactant.

EXAMPLES

Exemplary Compounds for Formulation in a Composition of the Invention

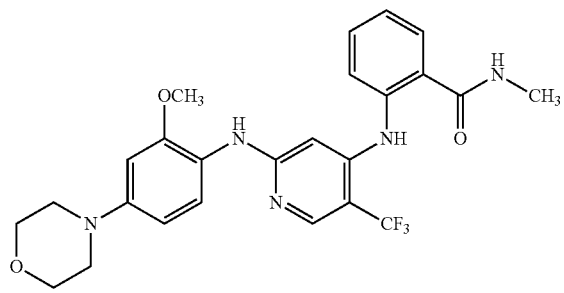

SR2516

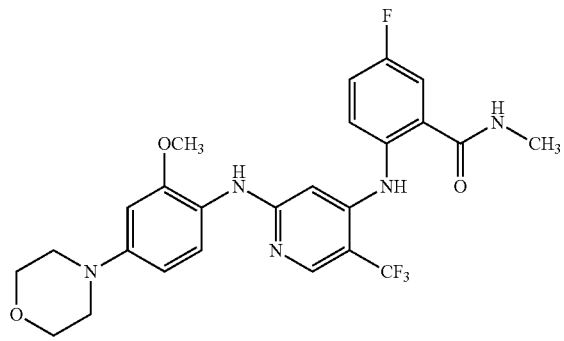

SR3406

Solubility of SR2516 and SR3406 in Selected Oils

This purpose of this study was to select an oil system as the vehicle base for the self-emosifying formulation based on the solubility

| Component | | | |
|---|---|---|---|
| Name | Grade | Vendor | Lot |
| SR-2516 | | Poniard | 07-00652 |
| SR-3406 | | poniard | 07-16643-S-1A |
| Miglyol 812 | EP | Sasol | 020201 |
| Capmul MCM | USP | ABITEC | 060429-7 |
| Labrafil M 1944 CS | EP | Gattefosse | 27715 |
| Castor oil | Food | Spectrum | UI0653 |
| Oleic acid | NF | Spectrum | 0A2-108 |
| Vitamin E acetate | USP | Roche | SJ1143 |

Compounding table (5% drug load)

| | Formulation | | | | | |
|---|---|---|---|---|---|---|
| Name | F-1 | F-2 | F-3 | F-4 | F-5 | F-6 |
| SR APIs | 25 | 25 | 25 | 25 | 25 | 25 |
| Miglyol 812 | 475 | | | | | |
| Capmul MCM | | 475 | | | | |
| Labrafil M 2125 | | | 475 | | | |
| Castor oil | | | | 475 | | |
| Oleic acid | | | | | 475 | |
| Vitamin E acetate | | | | | | 475 |
| Total | 500 | 500 | 500 | 500 | 500 | 500 |

Procedure
1. Add 25 mg of each API in 2 mL eppendoff vial. Record weight.
2. Weigh out each excipient. Record weight.
3. Beadbeater 100 sec to mix well. If all dissolved, add additional 5-10 mg each time until excess solid is present.
4. Use a platform shaker to shake all vials overnight at 25 deg C.
5. Observe for clarity, presence and relative amount of precipitates.
6. Filter using spin-X (0.22 um).
7. Dilute the filtrate to normal concentration for HPLC analysis for drug concentration and purity %.
8. Keep the filtrate at room temperature and observe for ppt at longer time point(s) if needed.

Results
Analysis on Filtrate Samples

| SR-2516* | | | | |
|---|---|---|---|---|
| ID | Excipient | Appearance | Solubility (mg/g) | Purity % |
| F1 | Miglyol 812 | Clear | 0.3 | 91.3 |
| F2 | Capmul MCM | Clear, light yellow | 8.4 | 98.9 |
| F3 | Labrafil M 1944 CS | Clear, light green | 2.2 | 98.1 |
| F4 | Castor oil | Clear, light green | 1.5 | 97.0 |
| F5 | Oleic acid | Clear, light gray | 5.8 | 99.0 |

*Purity of SR-2516 standard solution is 98.9%

| SR-3406* | | | | |
|---|---|---|---|---|
| ID | Excipient | Appearance | Solubility (mg/g) | Purity % |
| F1 | Miglyol 812 | Clear | 0.3 | 100.0 |
| F2 | Capmul MCM | Clear, light yellow | 13.6 | 98.5 |
| F3 | Labrafil M 1944 CS | Clear, light green | 1.0 | 95.4 |
| F4 | Castor oil | Clear, light green | 4.9 | 98.7 |
| F5 | Oleic acid | Clear light green | 0.4 | 100.0 |

*Purity of SR-3406 standard solution is 99.8%

This purpose of this study was to select an oil/surfactant system(s) capable of dissolving SRs to the target concentration

| Components | | | |
|---|---|---|---|
| Name | Grade | Vendor | Lot |
| SR-2516 | | Poniard | 07-00652 |
| SR-3406 | | Poniard | 07-16643-S-1A |
| Capmul MCM | USP | Abitech | 060429-7 |
| PL90G | EP | American Lecithin | 50660 |
| TPGS | EP | Eastman | 50053 |
| PEG400 | NF | Croda | 25322-68-3 |

| Composition % (w/w) | | | | | | | | |
|---|---|---|---|---|---|---|---|---|
| Name | F-B1 | F-B2 | F-B3 | F-B4 | F-C1 | F-C2 | F-C3 | F-C4 |
| SR-2516 | 5 | 5 | 5 | 5 | | | | |
| SR-3406 | | | | | 5 | 5 | 5 | 5 |
| Capmul MCM | 45 | 45 | 35 | 35 | 45 | 45 | 35 | 35 |
| PL90G | 25 | 20 | 35 | 30 | 25 | 20 | 35 | 30 |
| TPGS | 25 | 20 | 25 | 20 | 25 | 20 | 25 | 20 |
| PEG400 | | 10 | | 10 | | 10 | | 10 |
| Total | 100 | 100 | 100 | 100 | 100 | 100 | 100 | 100 |

| SR-2516* | | |
|---|---|---|
| ID | Solubility (mg/g) | Purity % |
| F-B1 | 50.1 | 99.0 |
| F-B2 | 49.2 | 98.7 |
| F-B3 | 46.4 | 99.0 |
| F-B4 | 48.6 | 98.9 |

*Purity of SR-2516 standard solution is 99.5%

| SR-2516 Appearance | | | |
|---|---|---|---|
| ID | Time 0 | Day 3 @ 2-8 deg C. | Day 7 @ 2-8 deg C. |
| F-B1 | Clear, bright yellow | Clear, darker yellow | Clear, darker yellow |
| F-B2 | Clear, bright yellow | Clear, darker yellow | Clear, darker yellow |
| F-B3 | Clear, bright yellow | Clear, darker yellow, 2 phases | Clear, darker yellow, 2 phases |
| F-B4 | Clear, bright yellow | Clear, darker yellow, 2 phases | Clear, darker yellow, 2 phases |

SR-3406*

| ID | Solubility (mg/g) | Purity % |
|---|---|---|
| F-C1 | 49.5 | 99.5 |
| F-C2 | 48.4 | 99.5 |
| F-C3 | 52.8 | 99.4 |
| F-C4 | 47.2 | 99.5 |

*Purity of SR-3406 standard solution is 99.0%

SR-3406 Appearance

| ID | Time 0 | Day 3 @ 2-8 deg C. | Day 7 @ 2-8 deg C. |
|---|---|---|---|
| F-C1 | Clear, yellow | Clear, yellow | Clear, yellow |
| F-C2 | Clear, yellow | Clear, yellow | Clear, yellow |
| F-C3 | Clear, yellow | Clear, yellow, 2 phases | Clear, yellow, 2 phases |
| F-C4 | Clear, yellow | Clear, yellow, 2 phases | Clear, yellow, 2 phases |

This purpose of this study was to evaluate the stability of SR-261 and SR-3406 at 5% in F-1 formulation for up to 2 weeks.

Components

| Name | Grade | Vendor | Lot |
|---|---|---|---|
| SR-2516 | | Poniard | 07-00652 |
| SR-3406 | | Poniard | 07-16643-S-1A |
| Capmul MCM | USP | Abitech | 060429-7 |
| PL90G | EP | American Lecithin | 50660 |
| TPGS | EP | Eastman | 50053 |
| PEG400 | NF | Croda | 25322-68-3 |

Composition % (w/w)

| | SR-2516 | | SR-3406 | |
|---|---|---|---|---|
| Excipients | % (w/w) | gm | % (w/w) | gm |
| SR API | 5 | 0.25 | 5 | 0.25 |
| Capmul MCM | 45 | 2.25 | 45 | 2.25 |
| PL90G | 25 | 1.25 | 25 | 1.25 |
| Vitamin E TPGS | 25 | 1.25 | 25 | 1.25 |
| Total | 100 | 5 gm | 100 | 5 gm |

Result

Time 0

| Formulation | % residual acetone | Appearance | PH* | concentration (mg/g) | Purity % |
|---|---|---|---|---|---|
| SR-2516 (F-B1) | 0.7 | Clear, dark yellow | 2.17 | 51.0 | 99.3 |
| SR-3406 (F-C1) | 0.9 | Clear, yellow | 2.69 | 50.5 | 98.8 |

*1:1 w/w dilution with DI-water

1-week

| Formulation | Storage Condition | Appearance | PH* | concentration (mg/g) | Purity % | Recovery % (over T0) |
|---|---|---|---|---|---|---|
| SR-2516 (F-B1) | −20° C./ambient RH | No change | 2.16 | 50.0 | 99.6 | 98.0 |
| | 5° C./ambient RH | No change | 2.14 | 49.6 | 99.8 | 97.1 |
| | 25° C./60% RH | No change | 2.10 | 51.4 | 98.0 | 100.7 |
| SR-3406 (F-C1) | −20° C./ambient RH | No change | 2.60 | 49.4 | 99.3 | 97.8 |
| | 5° C./ambient RH | No change | 2.71 | 51.3 | 99.1 | 101.8 |
| | 25° C./60% RH | No change | 2.70 | 49.7 | 98.9 | 98.5 |

*1:1 w/w dilution with DI-water

2-week

| Formulation | Storage Condition | Appearance | PH* | concentration (mg/g) | Purity % | Recovery % (over T0) |
|---|---|---|---|---|---|---|
| SR-2516 (F-B1) | −20° C./ambient RH | No change | 2.14 | 49.50 | 99.4 | 96.9 |
| | 5° C./ambient RH | No change | 2.14 | 50.39 | 98.8 | 98.7 |
| | 25° C./60% RH | No change | 2.18 | 51.52 | 97.9 | 100.9 |

-continued

| | | 2-week | | | | |
|---|---|---|---|---|---|---|
| Formulation | Storage Condition | Appearance | PH* | concentration (mg/g) | Purity % | Recovery % (over T0) |
| SR-3406 (F-C1) | −20° C./ ambient RH | No change | 2.65 | 49.50 | 99.4 | 95.9 |
| | 5° C./ ambient RH | No change | 2.67 | 50.39 | 98.5 | 94.1 |
| | 25° C./ 60% RH | No change | 2.71 | 51.52 | 96.4 | 94.4 |

*1:1 w/w dilution with DI-water

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An oral formulation for administration of a kinase inhibitor of the formula

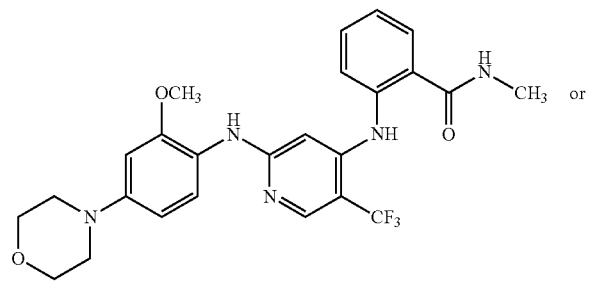

or

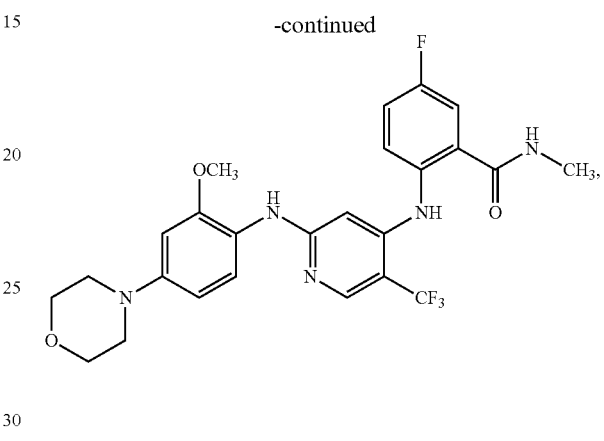

or any pharmaceutically acceptable salt thereof, comprising about 2 wt % to about 5 wt % of the kinase inhibitor, about 35-50 wt % of a glyceryl caprate/caprylate ester, about 20-40 wt % of a lecithin, about 15-30 wt % of an alpha-tocopheryl polyethylene glycol 1000 succinate, and up to about 10% PEG 400.

2. The formulation of claim 1 wherein the formulation is self-emulsifying.

3. The formulation of claim 2 wherein the formulation is self-emulsifying in the gastrointestinal tract of a patient ingesting the formulation.

4. The formulation of claim 3 wherein, after administered, the plasma exposure (AUC) is increased in the patient relative to the plasma exposure for a comparable dose orally administered in a non-self-emulsifying formulation.

* * * * *